United States Patent [19]
Chung et al.

[11] Patent Number: 5,401,805
[45] Date of Patent: Mar. 28, 1995

[54] OLEFIN GRAFT COPOLYMERS PREPARED USING BORANE-CONTAINING OLEFIN BACKBONE POLYMERS

[75] Inventors: T. C. Chung; G. J. Jiang; D. Rhubright, all of State College, Pa.

[73] Assignee: The Penn State Research Foundation, University Park, Pa.

[21] Appl. No.: 146,861

[22] Filed: Nov. 3, 1993

Related U.S. Application Data

[63] Continuation-in-part of Ser. No. 863,632, Apr. 6, 1992, Pat. No. 5,286,800.

[51] Int. Cl.$^6$ .................. C08F 255/00; C08F 279/02; C08F 289/00
[52] U.S. Cl. ..................................... 525/288; 525/268; 525/279; 525/296; 525/301; 525/309; 525/310; 525/317; 525/302; 525/316
[58] Field of Search ............... 525/288, 268, 279, 296, 525/301, 302, 309, 310, 317, 316

[56] References Cited

U.S. PATENT DOCUMENTS 5,247,023  9/1993  Chung et al. .......................... 525/288
5,286,800  2/1994  Chung et al. .......................... 525/288

FOREIGN PATENT DOCUMENTS 04-153237  5/1992  Japan .

*Primary Examiner*—Vasu S. Jagannathan
*Attorney, Agent, or Firm*—Thomas J. Monahan

[57] ABSTRACT

Graft copolymers are disclosed which comprise an olefin borane-containing homopolymer or copolymer backbone polymer having radically polymerized polymeric segments chemically bonded as side chains or as a chain end. A borane-containing diene homopolymer or a copolymer of a diene and/or at least one alpha-olefin having from about 2 to 22 carbon atoms copolymerized with another monomer containing organoborane functional groups can be used as a backbone polymer to prepare the graft copolymers of the present invention. Under oxidation conditions, the borane group becomes the reaction site for the radical polymerization and copolymerization. Radical polymerizable monomers, such as methyl methacrylate, styrene, alpha-methylstyrene, acrylonitrile and the like, can be polymerized to yield high molecular weight graft copolymer. By this synthetic route, high graft efficiency is observed with only a very low concentration of homopolymer being produced.

59 Claims, No Drawings

OLEFIN GRAFT COPOLYMERS PREPARED USING BORANE-CONTAINING OLEFIN BACKBONE POLYMERS

RELATED APPLICATION

This application is a continuation-in-part of application Ser. No. 863,632, filed on Apr. 6, 1992, now U.S. Pat. No. 5,286,800.

BACKGROUND OF THE INVENTION

1. Field of the Invention

This invention relates to graft copolymers. More particularly, the present invention relates to graft copolymers including an olefin and/or diolefin backbone polymer and a free radically polymerized polymer grafted thereto made using a borane-containing backbone polymer.

2. Description of Related Art

Although useful in many commercial applications, hydrocarbon polymers, such as olefins and/or diolefin homopolymers and copolymers suffer the major deficiency of poor interaction with other materials. The inert nature of such hydrocarbon polymers significantly limits their end uses, printability those in which adhesion, limits their end uses, particularly or compatibility with other functional polymers is paramount. The poor compatibility of such polymers is further evidenced in their use as coatings where weak adhesion between the polymers and metal surfaces has not allowed the facile use of these materials for the protection of metal. Furthermore, attempts to blend such hydrocarbon polymers with many other non-olefin-based polymers have been unsuccessful because of the incompatibility of the two types of polymers.

It has been demonstrated that the addition of polar groups to a hydrocarbon polymer structure can improve the adhesion thereof to many substrates, such as metals and glass. In polymer blends, the compatibility of the polymers can be improved by adding a suitable compatibilizer which alters the morphology of these blends. To be successful, it is necessary to reduce the domain sizes for both of the polymers and to increase the interaction between domains.

It is possible to use block or graft copolymers as compatibilizers in such situations as, for example, disclosed in U.S. Pat. No. 4,299,931; Macromolecules 15,370, 1982; Macromolecules 12,131, 1979; J. Polym. Sci, Polym Phys. 18, 2148, 1980; and U.S. Pat. No. No. 4,174,358. Most block copolymers have been produced by sequential living polymerization processes, particularly anionic polymerization, but such processes are limited to a relatively limited class of monomers. A number of the techniques used to produce these graft or block copolymers are inefficient, resulting in ill-defined products caused by gel formation, backbone degradation, the formation of homopolymers, uncontrolled graft density and molecular weight. These deficiencies are even more pronounced for polyolefins due to their inert nature and difficulties in functionalization reactions involving such polymers. As a consequence, polyolefins have been the most difficult materials to chemically modify, both by functionalization and graft reactions.

This inertness may be overcome to some extent by incorporating polar (functional) groups into polyolefin materials and several techniques for accomplishing this are known. One technique involves oxidizing the polymer backbone by irradiation or contact with a free radical generator (organic peroxide) and then contacting the activated polymer with an unsaturated polar compound such as maleic anhydride. However, such processes can lead to degradation of the polymer backbone during the treatment process. Another technique involves forming copolymers of alpha olefin monomers and copolymerizable monomers containing polar groups.

Among the polyolefins, polypropylene is generally more difficult to functionalize by copolymerization processes. Because crystalline polypropylene is made only using Ziegler-Natta catalyst, it is generally difficult to impart functionality to the polymer by copolymerization techniques because polar groups present in the comonomers tend to be reactive with the catalyst system, rendering the catalyst inactive and poisoning it. U.S. Pat. No. 3,492,277 discloses prereacting a polar monomer such as undecylenic acid, alcohol or amide with an organo aluminum compound thereby rendering such monomers less reactive with Ziegler catalysts. This facilitates their use in forming Ziegler catalyzed alpha olefin copolymers. A similar technique is disclosed in U.S. Pat. No. 4,518,757 wherein copolymers are prepared comprising an alpha olefin and an acid ester comonomer such as methyl-10-undecenoate ester. More recently, versatile homopolymers and copolymers based on borane-containing monomers have been disclosed. U.S. Pat. Nos. 4,734,472 and 4,751,276 disclose borane-containing monomer material prepared by reacting a diolefin and a dialkyl borane solution. These monomers may be polymerized using Ziegler-Natta catalysts to form polyborane homopolymers or random copolymers of 1-octene and the borane-containing monomer.

Block or blocky copolymers of propylene and such borane-containing monomers are the subject of copending application Ser. No. 07/637,410, filed on Jan. 4, 1991.

The chemistry involved in the above-mentioned patents and application is the direct polymerization using organoborane-substituted monomers and alphaolefins in Ziegler-Natta processes. The homo- and copolymers containing borane groups are very useful intermediates to prepare a series of functionalized polyolefins. The essential advantages of this chemistry are (a) the stability of the borane moiety to transition metal catalysts, (b) the solubility of borane compounds in hydrocarbon solvents (hexane and toluene) used in transition metal polymerizations, and (c) the versatility of borane groups which can be transformed to a wide variety of functionalities, as discloses by H. C. Brown, Organic Synthesis via Boranes; Wiley-Interscience; New York, 1975. Many new functionalized polyolefins with various molecular architectures may be obtained based on this chemistry.

It is also known that trialkyborane in an oxidated state becomes an initiator for the polymerization of a number of vinyl monomers, as disclosed by J. Furukawa et al., J. Polymer Sci, 26, 234, 1957; J. Polymer Sci. 28,227, 1958; Makromol. Chem., 40, 13, 1961; F. J. Welch, J. Polymer Sci. 61,243, 1962; and in U.S. Pat. No. 3,476,727. The polymerization mechanism involves free radical addition reactions. The initiating radicals may be formed from homolysis of peroxyborane or by the redox reaction of the peroxyborane with unoxidized trialkylborane. A major advantage in borane initiators is the ability to initiate polymerization at low temperature. Peroxides and azo initiators when used alone usually require considerable heat input to decompose and thereby to generate free radicals. Elevation of the reaction temperature often causes significant reduction in polymer molecular weight accompanied by the loss of important properties of the polymer.

U.S. Pat. No. 3,141,862 discloses conducting a trialkylborane-initiated free radical polymerization in the presence of a polyolefin polymer. Apparently, the graft reaction by this route was very difficult. The inert nature and insolubility of polyolefin (due to crystallinity) also seems to have hindered the process and resulted in very poor graft efficiency. The reactions shown in the examples of this patent also seem to require a very high concentration of organoborane initiator and monomer and require elevated temperature. The majority of the products are homopolymers or insoluble gel. No information about he molecular structure of the copolymer is given. Despite the advantages of borane initiators, organoborane-initiated polymerizations tend to be unduly sensitive to the concentration of oxygen in the polymerization system. Too little or too much oxygen results in little or no polymerization. High oxygen causes organoborane to be rapidly transferred to borinates, boronates and borates which are poor initiators at low temperatures. Moreover, polymerization is often inhibited by oxygen. To facilitate the formation of free radicals, U.S. Pat. Nos. 4,167,616 and 4,638,092 discloses that borane containing oligomers and polymers may be used as initiators in such free radical polymerizations. These organoboranes are prepared by the hydroboronation of diene monomer or polymers or copolymers. The similar polymeric organoborane adduct, prepared by the hydroboronation of 1,4-polybutadiene and 9-borabicyclo-(3,3,1)-nonane has also been reported in Macromol. Chem. 178, 2837, 1977. However, no information was provided about the applications of organoborane-containing polyolefin polymers in the preparation of polyolefin graft copolymers.

SUMMARY OF THE INVENTION

In this invention, new graft copolymers have been discovered which comprise a homopolymer or copolymer backbone polymer having at least one and preferably a plurality of free radical polymerized polymeric segments chemically bonded as side chains and/or chain ends. Most particularly in accordance with this invention, it has been found that the use of a hydrocarbon polymer which has been modified to contain organoborane units can be used as a backbone polymer to prepare the graft copolymers of the present invention. The hydrocarbon polymers may include, for example, homopolymers or copolymers of at least one $C_2$ to $C_{22}$ monoolefin or homopolymers or copolymers of diolefins, such as butadiene, isoprene, cyclopentadiene or the like. Under oxidation conditions, the borane units become the reactive sites for the free radical polymerization and copolymerization. Numerous free radically polymerizable monomers, such as ethylene, methyl methacrylate, styrene, alpha-methylstyrene, acrylonitrile and the like can be polymerized and grafted to the backbone polymer at the reactive sites to yield high molecular weight graft copolymers. By this synthetic route, high graft efficiency is observed with only a very low concentration of homopolymer being produced.

DETAILED DESCRIPTION OF THE INVENTION

In one aspect, the graft copolymers prepared in accordance With this invention may be characterized by formula I as follows:

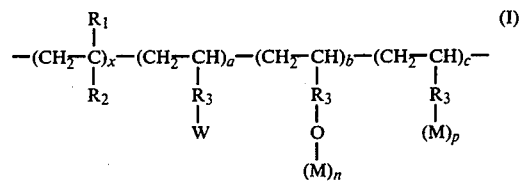

wherein $R_1$ and $R_2$ are the same or different and are selected from the group consisting of H, $C_1$ to $C_{20}$ linear or branched alkyl, phenyl and alkyl substituted phenyl; $R_3$ is a direct linkage or a divalent hydrocarbon having from 1 to 20 carbon atoms of linear or branched structure, preferably having the structure $-(CH_2)_m-$ wherein m is from 3 to about 10, most preferably from about 4 to about 6; W is a polar substituent group; M is the residue of a free radically polymerizable monomer; n and p are the same or different and are the degree of polymerization of M ranging from 1 to about 70,000; x ranges from about 50 to about 70,000, preferably from about 1,000 to about 70,000; (a) ranges from 0 to about 20,000, preferably from about 0 to about 100; (b) ranges from 1 to about 20,000, typically from about 1 to about 100; (c) ranges from 0 to about 20,000, typically from 0 to about 100; and the sum of (b) and (c) ranges from 1 to about 20,000.

In another aspect, the graft copolymers prepared in accordance with this invention may be characterized by the formula II as follows:

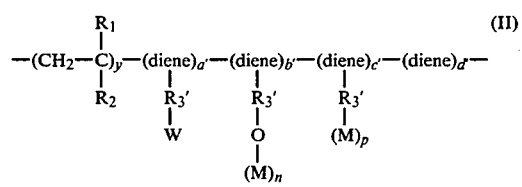

where $R_1$ and $R_2$, W, M, and n and p are as described above in connection with formula I; $R_3'$ is a direct link or a divalent hydrocarbon having from 1 to 20 carbon atoms of linear, cyclic or branched structure; (diene) is a recurring segment of a polymerized diolefin monomer; y ranges from 0 to about 70,000 typically from at least 1 to about 70,000, (a') ranges from 0 to about 20,000, preferably from 0 to about 100; (b') ranges from 1 to about 20,000, typically from 1 to about 100; (c') ranges from 0 to about 20,000, typically from 1 to about 100, (d') ranges from 0 to about 70,000, typically from 1 to about 70,000; and the sum of (b') and (c') is at least 1 and up to about 20,000, typically from 1 to about 100. In accordance with this aspect of the invention, when y is 0, the backbone polymer comprises a diene homopolymer or copolymer which is free from any segments derived from a monoolefin.

In yet another aspect, the graft copolymer may be characterized by the formula III as follows:

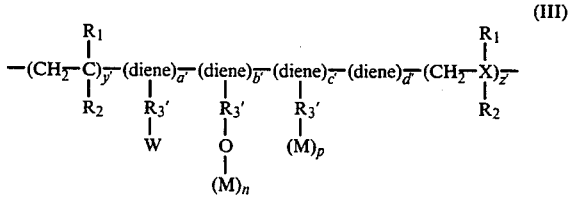

where $R_1$, $R_2$, $R_3'$, (diene), M, n, p, (a'), (b'), (c'), (d') and the sum of (b') plus (c') are as described above in connection with formula II; and y' and z' are the same or different and each ranges from about 100 to about 50,000.

It is to be understood from the above formulas that not all of the (b), (c), (b') and/or (c') segments of the polymer chain contain graft-chains attached thereto, in which case the graft copolymers will contain some (a) or (a') segments as well. Polar group W is preferably selected from the group consisting of OH, $NH_2$, CHO, halogen and $BR_4R_5$, wherein $R_4$ and $R_5$ are the same or different alkyl or cycloalkyl groups containing from 1 to about 10 carbon atoms. These groups may serve as a crosslinking site involving crosslinking reactions between the graft copolymers with themselves or with other functionalized polymers.

The reactive backbone of these graft copolymers may be prepared by either of two processes. Backbone polymers corresponding to formula I above may be prepared by direct copolymerization of a borane-containing monomer with one or a mixture of alpha-monoolefins using a Ziegler-Natta catalyst system. Backbone polymers responding to formulas II and III above are prepared by reacting a preformed polymer containing residual unsaturation along the polymer chain with a hydroboronation agent.

The borane-containing monomers which are useful in preparing the backbone copolymer of formula 1 above may be generally categorized by the formula:

wherein m is an integer ranging from 3 to 12, and $R_4$ and $R_5$ are the same or different alkyl or cycloalkyl groups containing 1 to 10 carbon atoms. This monomer may be prepared, for example, as the addition product of 9-borobicyclononane (hereinafter referred to as 9-BBN) and a diene having the structure

wherein z ranges from 1 to 10. Preferred dienes are those wherein z ranges from about 1–4 and include 1,7-octadiene, 1,5-hexadiene and 1,4-pentadiene, with 1,5-hexadiene being most preferred. The reaction is preferably conducted at a temperature of from about $-10°$ to $50°$ C. by slow addition of a solution of 9-BBN in suitable solvent such as tetrahydrofuran (THF) to a 2–6 molar excess of the diene material under an inert blanket such as argon or nitrogen, and allowing the reaction to proceed under mild agitation for a period of at least about 1 hour, preferably at least about 2–5 hours.

These monomers and the methods of synthesis are also disclosed in U.S. Pat. No. 4,751,276, the disclosure of which is incorporated herein by reference.

Monoolefins which may be copolymerized with the borane-containing monomers include one or a mixture of $C_2$ to $C_{20}$ olefins, preferably alpha-olefins such as ethylene, propylene, 1-butene, isobutene, 1-hexane, 1-octene and the like. Styrene and alpha-methylstyrene also may be copolymerized with the borane-containing monomers in accordance with this invention.

The direct copolymerization is usually carried out by a Ziegler-Natta process by mixing the olefin monomer and borane monomer with Ziegler-Natta catalyst. The preferred borane monomers include but are not limited to B-(7-octen-1-yl)-9-BBN; B-(5-hexen-1-yl)-9-BBN; and B-(4-penten-1-yl)-9-BBN. The Ziegler-Natta catalyst employed may include halides or alkoxyhalides of a transition metal, such as titanium, zirconium, vanadium, chromium and molybdenum, and a cocatalyst such as triethylaluminum, diethylaluminum chloride and ethylaluminum dichloride. The polymerization is usually carried out between $0°$ to $50°$ C., either neat or in hydrocarbon solvents such as hexane, heptane and toluene. The level of incorporation of the borane monomer into the resulting copolymer may range from 0.1 to 50% by mole, preferably from 0.1 to 5% by mole.

Polymers of formulas II and III above are prepared by the hydroboronation of preformed polymers containing residual unsaturation along the polymer chain. Examples of backbone polymers which may be hydroboronated in accordance with the invention include homopolymers of conjugated or non-conjugated dienes such as butadiene, isoprene or the like, norbornadiene, dicyclopentadiene, 1,4-hexadiene, 5-methylene-2-norbornene, 5-ethylidene-2-norbornene and the like materials.

Copolymers of styrene and/or alpha-methylstyrene with one or more conjugated or non-conjugated dienes also may be hydroboronated. These polymers are generally elastomeric in nature and include such materials as polybutadiene, poly(styrene/butadiene/styrene), poly(styrene/isoprene/styrene), isobutylene/isoprene copolymers (butyl rubber) and terpolymers of ethylene/propylene and a nonconjugated diene such as 1,4-hexadiene or 5-ethylidene-2-norbornene.

The hydroboration can also be applied to polymers having residual unsaturation at the chain end, which is usually the result of $\beta$-proton elimination during the termination. In these cases, the graft copolymers have the molecular structure illustrated in formula I, with an $(M)_n$ or $(M)_p$ moiety grafted at the chain end.

Hydroboronation reagents which may be used to prepare the hydroboronated polymer include boron hydride species such as diborane, 9-BBN, dimethyl borane, dichloroborane, catecholborane and other species which are reactive to double bonds and which are disclosed, for example, in U.S. Pat. No. 4,167,616 or in U.S. Pat. 4,638,092, referred to above.

Hydroboronation may be readily carried out by dissolving the elastomeric polymer in suitable solvent, adding stoichiometric or larger quantities of the hydroboronation reagent to the solution and heating the solution to effect reaction of the hydroboronating reagent with at least some of the double bonds present in the polymer backbone. The subsequent graft polymerization reaction is a free radical polymerization initiated by simultaneously exposing at least one monomer which is polymerizable by a free radical polymerization process and the borane-containing backbone polymer to controlled amounts of radical catalyst capable of converting the borane groups to free radicals which, in turn, are capable of initiating the graft polymerization. Preferably, the free radical catalyst comprises an oxidative reagent, including but not limited to oxygen, air, H₂O₂, cumene hydroperoxide, t-butylhydroperoxide and metal oxides. such as CuO, MnO₂ and V₂O₅. In a preferred aspect of the invention, oxygen or air is used as the oxidative agent.

The preferred amount of oxidative reagent is stoichiometric to the borane groups present in the backbone polymer. The free radical polymerization may be carried out at a temperature between 0° to 80° C., preferably from about 0° to 30° C., neat or in common solvents such as THF, diethyl ether, cyclohexane, heptane, benzene and toluene. The oxidative reagent, for example, dry O₂, preferably is added slowly to the reaction mixture over the course of the graft polymerization reaction to ensure proper conversion of the borane groups in the borane-containing backbone polymer into free radicals which, in turn, can initiate the free radical polymerization.

Possible conversion routes for the borane groups into free radicals may be illustrated by the following series of schematic equations in which O₂ represents. dry oxygen which is injected slowly into the reaction mixture, e.g., at a final B:O ratio of from about 1:0.01 to about 1:10, preferably about 1:1, but with less than 10% of the oxygen being added hourly, at room temperature, and in which

represents the residue of alkyl-9-borabicyclo-(3,3,1)-nonane:

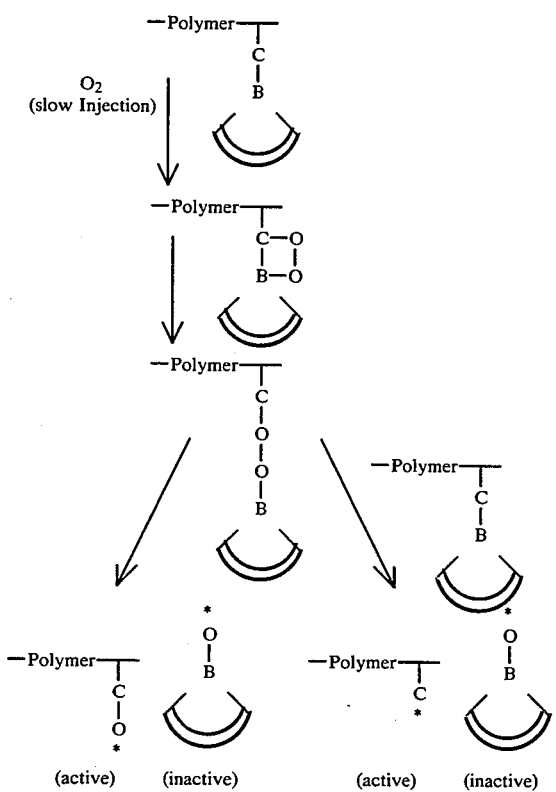

Free radically polymerizable monomers which may be used as the grafting monomer include, but are not limited to vinyl monomers such as alkyl acrylates and methacrylates, including methyl and tert-butyl methacrylates and acrylates; acrylic and methacrylic acids; vinyl aromatic compounds such as styrene, alpha-methylstyrene, para-methylstyrene, vinyl toluene and its isomers; vinyl amides such as acrylamide and methacrylamide; vinyl pyridine; acrylonitrile; methacrylonitrile; vinyl acetate; vinyl chloride, and vinylidene chloride. Polymerizable olefin monomers such as ethylene may also be used.

The graft polymerization process may be depicted as follows:

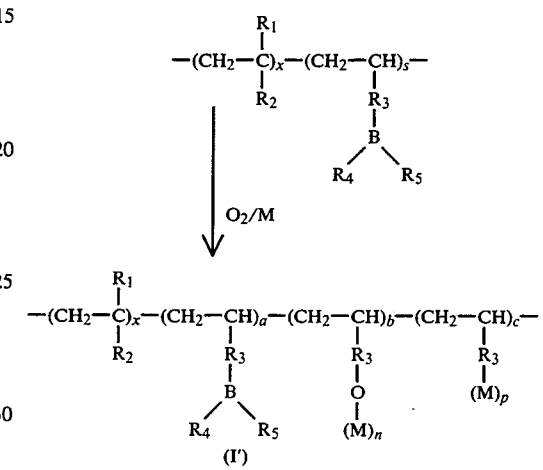

wherein x and s represent the number of monomer repeating units and s is equal to the sum of (a)+(b)+(c), and R₁, R₂, R₃, R₄, R₅, M, n, p, x, (a), (b) and (c) are as the same as set forth above. The graft polymerization also may be depicted as follows:

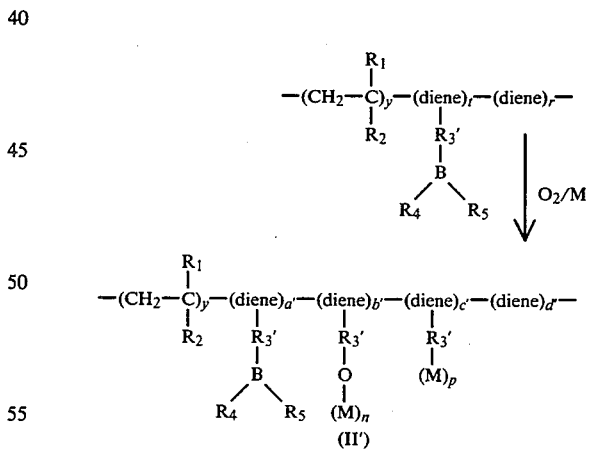

wherein y, t and r represent the number of monomer repeating units and the sum of t+r is equal to the sum of (a')+(b')+(c')+(d'), and R₁, R₂, R₃, R₄, R₅, (diene), y, (a'), (b'), (c'), (d'), M, n and p are as set forth above. In accordance with this aspect of the invention, when y is 0, the backbone of the graft copolymer is free from any segments that are derived from a monoolefin.

In yet another embodiment, the graft polymerization may be depicted as follows:

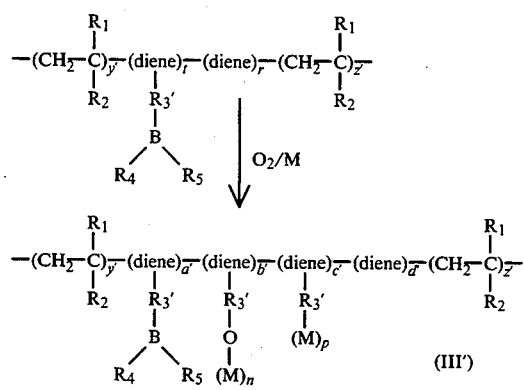

wherein y', t, r and z' represent the number of monomer repeating units and the sum of t+r is equal to the sum of (a')+(b')+(c')+(d') and R$_1$, R$_2$, R$_3$, R$_4$, R$_5$, (diene), y', (a'), (b'), (c'), (d'), z', M, n and p are as set forth above.

Graft copolymers in accordance with this invention may be prepared having a number average molecular weight (Mn) in the range of from about 50,000 to about 3,000,000, preferably from about 75,000 to 1,500,000 and more preferably from about 100,000 to about 1,000,000. The graft density of the side chains (number of graft chains per molecule of backbone polymer) will vary from between 0.1 to about 75% per backbone monomer repeating unit as a function of the mole % of organoborane repeating units present in or introduced into the backbone polymer. In addition, the Mn of the grafted side chains may range from about 500 up to about 500,000. As a general rule, it is preferred that where the graft density of side chains is below 1%, then the molecular weight of the side chains be above about 10,000; where the graft density of the side chains is above about 10%, then the molecular weight of the side chains is below about 2,000.

The preferred content of free radically polymerized graft polymer present in the copolymers generally may range from about 5 to about 95% by weight based on the total copolymer weight, with about 10 to about 80% by weight being the most preferred range.

As previously indicated, graft polymers having the structure I', II' and III' immediately above wherein (a) or (a') is at least 1 can be readily converted into graft polymers having the structure I, II, and III shown earlier wherein (a) or (a') is at least 1 by reaction with an appropriate reagent under mild conditions to introduce a polar substituent W into the polymer chain. Preferred polar substituents include OH, halogen such as iodine, CHO and NH$_2$. For example, the borane-containing copolymer, suspended in solvent, can be reacted with a mixture of an organic base and a peroxide to form alcohol substituent groups displacing the borane radical. Similarly, polymers containing amino functionality may be prepared by reaction of the borane-containing polymer with NH$_2$OSO$_3$R; polymers containing aldehyde functionality may be prepared by reaction of the borane-containing polymer with a mixture of CO and K(i-C$_3$H$_7$O)$_3$BH; and polymers containing iodine functionality may be prepared by reaction of the borane-containing polymer with a basic solution of NaI/chloramine-T hydrate. Other such reactions are disclosed by Brown, H. C., Organic Synthesis via Boranes; Wiley-Interscience: New York, 1975, the relevant portions of which are incorporated herein by reference.

Unmodified borane-containing polymers of the formula I, II or III above wherein W is B-R$_4$R$_5$ can utilize the borane groups as crosslinking sites by exposing the borane-containing graft copolymer to a large excess of oxidative reagent such as air or peroxides. This process can be completed in-situ during the grafting reaction. In such a case the polymers become crosslinked by intermolecular linkages at the W sites.

Graft polymers prepared in accordance with this invention have a number of uses. They are soluble in many organic solvents and can be shaped into films or fibers. They may be used as compatibilizers for polymer systems based on olefin and/or diolefin polymers blended with other polymers with which the olefin and/or diolefin polymers are not normally compatible such as polyamides, vinyl aromatic polymers, polyesters and similar polar polymers. They also find utility as adhesives to promote interfacial bonding between olefin and/or diolefin polymer sheets, films or fibers and substrates such as other polymeric surfaces, glass, aluminum and other metals to which olefin and/or diolefin polymers do not readily adhere.

The graft copolymers may also be used to enhance the bonding between polymer matrix systems and reinforcing fillers and fibers such as carbon black and carbon or glass fibers. Inclusion of minor amounts of these graft copolymers in a polymer matrix with which the copolymers are compatible promotes good adhesion of the matrix system to fiber or filler by virtue of the polar nature of the polymer segments present in the graft copolymer side chains.

The following examples are illustrative of the invention.

EXAMPLE 1

Synthesis of hexenyl-9-BBN

The reaction is based on the monohydroboronation of 1,5-hexadiene. In an argon filled dry box, 15.092 g (0.124 moles) of 9-BBN dimer crystals were dissolved in 100 ml of dry-degassed THF and added dropwise over 2 hours to 44.515 g (0.542 moles) of 1,5 hexadiene. The solution was stirred at room temperature for 12 hours before any unreacted diene and the THF were removed under vacuum. Another 10.754 g (0.088 moles) of 9-BBN were added to the isolated hexadiene and THF solution as before. Again after 12 hours the unreacted diene and the remaining clear oil fractions were combined and distilled under vacuum. The second fraction collected at 68° C. at 11 mm Hg was a clear sightly viscous liquid which proved to be pure hexenyl-9-BBN by $^1$H and $^{11}$B NMR. 36.01 g were collected for a 73.1% yield.

EXAMPLE 2

Synthesis of polyoctene-co-hexenyl-9-BBN

In a typical example, a half liter flask was charged with Ziegler-Natta catalyst, TiCl$_3$.AA (0.08 g, 0.4 mole) and AlEt$_2$Cl (2.5 mole, 0.3 g) and toluene (50 ml) under argon atmosphere. After aging for 30 min with sufficient mixing, the monomer mixture of 1-octene (11.2 g) and 1-hexenyl-9-BBN (0.101 g) in 150 ml of toluene, monomer mole ratio of 1000 to 5, was added to the catalytic solution. The copolymerization reaction was observed within 5 minutes with visible increase in viscosity. The solution was stirred at room temperature for one hour before the reaction was terminated with isopropanol (300 ml). The precipitate was collected by filtration, washed with isopropanol three times and vacuum dried overnight to yield 5.1 g of copolymer. Trialkylborane in the copolymer was characterized by $^{11}B$ NMR with chemical shift sigma=87 ppm from $BF_3OEt_2$. A total of six different copolymers, polyoctene-co-hexenyl-9-BBN, were prepared by these procedures and are identified as A1 through A6 in Table 1.

TABLE 1

Summary of the Copolymerization of 1-octene and 1-hexenyl-9-BBN

| Sample Number | Monomer Feed (mole ratio) | Reaction** Time (min) | Borane*** (mole %) | Product/Copolymer yield (%) | Mn × $10^{-3}$ | Mw/Mn |
|---|---|---|---|---|---|---|
| A1 | 1,000/5 | 30 | 0.2 | 45 | 320 | 6.3 |
| A2 | 100/1 | 20 | 0.4 | 34 | 310 | 5.8 |
| A3 | 4/1 | 20 | 5 | 20 | 280 | 6.5 |
| A4 | 3/1 | 120 | 15 | 60 | 242 | 6.1 |
| A5 | 1/1 | 120 | 40 | 55 | 126 | 7.8 |
| A6 | 1/3 | 120 | 65 | 52 | 66 | 6.0 |

*octene/1-hexenyl-9-BBN
**room temperature reaction
***mole % of borane monomer

The analysis of the above organoborane-containing copolymers, such as borane concentration and molecular weight concentration and molecular weight of copolymer, was done in their corresponding hydroxylated copolymer form. The oxidation reaction was carried out by dissolving the organoborane-containing copolymer in THF solution. After adding 6N sodium hydroxide, hydrogen peroxide (30%) was dropped in over a period of 15 minutes. After stirring the mixture at 55° C. for half hour, water was added and the precipitate was collected by filtration and washed with water. Further purification was carried out by redissolving the copolymer in THF, reprecipitating by acetone and drying in vacuum overnight to obtain the desired product. In $^1H$ NMR spectrum, the integrated intensity between the chemical shifts sigma=3.6 ppm ($CH_2O$) and sigma=0-.8-2 ppm (rest of protons in the copolymer) offer the functional group concentration in the copolymer.

EXAMPLE 3

Preparation of Polyoctene-q-PMMA

The polyoctene-co-hexenyl-9-BBN copolymer of Example 2, sample A1, was used to prepare polyoctene-g-polymethylmethacrylate (Polyoctene-g-PMMA) graft copolymer by a free radical graft-from reaction. In a nitrogen atmosphere, 2 g of copolymer A1, dissolved in 50 ml of THF, was mixed with 50 ml of pure methylmethacrylate (MMA) monomer in a 200 ml flask. A septum was installed to the flask to isolate the mixture from air. The graft-from reaction occurred after injecting 5 ml of air into the flask by syringe. A notable increase in solution viscosity was observed within a few minutes. The reaction mixture was stirred at ambient temperature and became very sticky after one hour. About 1 ml of reaction mixture was sampled and injected into 10 ml of isopropanol. The resulting precipitate was collected by filtration. Additional washing with isopropanol was continued three times. To remove the possible polymethylmethacrylate (PMMA) homopolymer in the precipitate, a solvent extraction procedure was carried out using acetone solvent. Almost no PMMA homopolymer was extracted out after stirring the mixture at room temperature for 24 hours. The product was then dried in vacuum overnight yielding a graft copolymer which was very soluble in THF solvent. Based on the IR and $^1H$ NMR studies, the graft copolymer consisted of 50 mole % of PMMA side chains. The graft-from reaction was continued by redissolving this polymer in THF and continuing the polymerization as described above for two hours before exposing the mixture to ambient atmosphere. The product was precipitated by adding 100 ml of isopropanol. The same purification processes to remove impurities and PMMA homopolymer were repeated as above to obtain 42 g of Polyoctene-g-PMMA with 75 mole % of PMMA side chains in the copolymer.

The detail molecular structure of Polyoctene-g-PMMA was measured by IR, $^1H$ NMR and GPC techniques. IR spectrum showed a strong $V_{c=o}=1720$ $cm^{-1}$ peak, corresponding to carbonyl groups in PMMA. The quantitative analysis was obtained by $^1H$ NMR spectrum, the integrated intensity comparison between the chemical shifts sigma=3.6 ppm ($CH_3$—O) and sigma=0.8-2 ppm (rest of copolymer) offers the PMMA concentration in the Polyoctene-g-PMMA copolymer. The average chain length of PMMA in the side chain of the graft copolymer can be estimated by the weight increase during the graft from reaction divided by the moles of organoborane groups in the starting polyoctene-co-hexenyl-9-BBN copolymer. Assuming all organoborane groups are involved in the polymerization, the average molecular weight of PMMA is above 60,000 g/mole.

The thermal properties of the copolymer were evaluated by DSC measurement. DSC curve of Polyoctene-g-PMMA copolymer (with 50 mole % of PMMA) shows two glass transition temperatures (Tg) −58° C. and 113° C., corresponding to the glass transition temperatures of the two homopolymers respectively. This data indicates a phase separation in the copolymer and that the polymer chain length in both polymer segments is quite long resulting in the formation of polyoctene and PMMA domains.

EXAMPLE 4

Preparation of Polyoctene-q-PMMA

Following the general procedure set forth in Example 3, sample A2 in Example 2, which has a 0.4 mole % content of hexenyl-9-BBN in the copolymer, was used to prepare a graft copolymer of Polyoctene-g-PMMA. Two processes of introducing air to the reaction mixture were carried out to study the graft-from reaction. (a) Slow diffusion of air into the reaction system In a 200 ml flask, sample A2 (1 g) was dissolved in 70 ml of THF, then 3 ml of pure MMA was added. The graft polymerization took place under very slow diffusion of air through the septum. Air was leaked into the reactor very slowly and the formation of the free radical was also very slow. After one day at ambient temperature, 1 ml of reaction mixture was sampled and purified by the same procedures described in Example 3. The resulting graft copolymer was found to consist only of 2 mole % of PMMA. Under the same reaction condition for two days, about 8 mole % of PMMA was observed in copolymer. After five days reaction time, 30 mole % of PMMA was grafted to the copolymer. In all samples, an almost undetectable amount of PMMA homopolymer could be extracted out by acetone solvent. The graft copolymers were also soluble in THF solvent. The graft-from reaction was obviously continuing during the entire process with slowly increasing levels of oxygen being introduced into the reactor.

(b) Expose the reaction system to air

Preparing the same reaction mixtures as described above, sample A2, MMA and THF were mixed in a 200 ml flask. The system was, however, immediately exposed to air. After 10 minutes at room temperature, the sampled polymer was analyzed to have 10 mole % of PMMA, which increased to 16 mole % PMMA after another 10 minutes.

EXAMPLE 5

Preparation of Polyoctene-q-PMMA

Following the procedure set forth in Example 3, sample A3 in Example 2, which has 5 mole % of hexenyl-9-BBN in the copolymer, was used to prepare the graft copolymer of Polyoctene-g-PMMA. The borane containing polymer (0.73 g) was dissolved in 100 ml of THF. 3 ml of pure MMA (MMA/Borane=50/1) was added to the copolymer solution. The graft polymerization took place under slow diffusion of $O_2$ from air through the airtight septum. After 2 hrs, the reaction was terminated by pumping out the MMA and solvent in the vacuum line. 1.57 g of PMMA grafted copolymer was obtained. The unreacted borane in the copolymer was oxidized to hydroxyl groups by $NaOH/H_2O_2$ to obtain a grafted copolymer containing 10 mole % of PMMA.

EXAMPLE 6

Preparation of Polyoctene-q-PMMA

Following the procedure set forth in Example 3, sample A3 in Example 2, which has 5 mole % of hexenyl-9-BBN in the copolymer, was used to prepare the graft copolymer of Polyoctene-g-PMMA. The borane containing copolymer A3 was dissolved in 50 ml of THF before adding 6.62 g of purified MMA (77 mole) (MMA/Borane=10/1). The graft polymerization took place under slow diffusion of $O_2$ from air through the septum. The reaction was held at room temperature overnight. After one day, 25 ml of air was injected into the solution mixture and reacted for one more day. The unreacted borane in the copolymer was oxidized to hydroxyl groups by $NaOH/H_2O_2$ reagents. Some of the product formed microemulsion in the aqueous phase. The precipitated portion (about ⅓) contained about 15% by weight of PMMA. The rest (about ⅔) forming a microemulsion in water was isolated by adding NaCl into the solution. The graft copolymer obtained in this portion had a PMMA concentration of about 60% by weight.

EXAMPLE 7

Copolymerization of Polypropylene and Hexenyl-9-BBN

Propylene gas (Matheson research grade) was dried over NaOH and $P_2O_5$ columns before condensing into a graduated Schlenk flask containing 0.50 ml of $AlEt_2Cl$ at $-78°$ C. 16.9 ml of propylene (10.96 g, 0.261 moles) was transferred to a 1000 ml Schlenk flask containing 500 ml of toluene. After warming to room temperature, the flask was brought into a dry-box and contacted with 5.312 g ($2.602\times10^{-2}$ moles) of hexenyl-9-BBN. 30 ml of aged (½ hour) catalysts slurry containing 0.619 g ($4.1\times10^{-3}$ mol) of $TiCl_3$-AA and 2,988 g ($2.48\times10^{-2}$ mol) $AlEt_2Cl$ was added to catalyze the copolymerization. The polymerization was terminated after 30 minutes by the addition of isopropyl alcohol. The polymer was isolated by the addition of cold isopropanol followed by filtration. The white powder was then dried under vacuum to yield 5.778 g of poly(propylene-co-hexenyl-9-BBN) which had about 1 mole % hexenyl-9-BBN in the copolymer.

EXAMPLE 8

Copolymerization of Propylene and Hexeny-9-BBN in Continuous Reaction

In an argon filled dry box, 15.477 g of 5-hexenyl-9-BBN and 200 ml of hexane were placed in a Parr 450 ml stirred pressure reactor and sealed. Outside the box, 8.20 g of propylene was added under $N_2$ pressure. A slurry of 1.027 g of $TiCl_3$.AA and 4.705 g of $AlEt_2Cl$ in 100 ml of toluene was then added under $N_2$ pressure to catalyze the copolymerization. Additional propylene was added at 30 minute intervals with 7.20, 6.40, 5.60 and 4.00 g of propylene being added at respective intervals. After the last monomer charge, the reaction was performed for an additional hour before being terminated by injection of 100 ml of isopropanol. The reactor was stirred for an additional ½ hour before being vented of the excess pressure and being placed into the box for further purification with IPA. The resulting polypropylene (sample B2 in Table 2) contains about 3 mole % of borane groups. The same reactions were repeated for samples B2 and B3, but the feed ratios and reaction times were changed. The results are summarized in Table 2.

TABLE 2

Summary of Copolymerization of Propylene and Hexeny-9-BBN by Continuous Reaction.

| Sample number | % B* in Feed | % B in Polymer | Reaction Time (hr.) | Yield (%) | $\eta$** | Mv (g/mole) |
|---|---|---|---|---|---|---|
| B1 | 1.5 | 0.5 | 2 | 85 | 1.97 | 215,000 |
| B2 | 10 | 3 | 3 | 62 | 1.78 | 183,000 |
| B3 | 13 | 5 | 3 | 55 | 1.71 | 174,000 |

*5-hexenyl-9-BBN
**intrinsic viscosity

EXAMPLE 9

Hydroboration of poly(propylene-co-1,4-hexadiene) with 9-BBN

In an argon filled dry box, 0.550 g of inhibitor-free poly(propylene-co-1,4-hexadiene) containing 1.7% of 1,4-hexadiene was placed in a suspension of 25 ml of dry toluene. A solution of 0.069 g of 9-BBN in 15 ml of dry THF was added to the polymer suspension. The suspension was heated to 65° C. in a flask equipped with a condenser. After stirring for 5 hours, the polymer was precipitated into 150 ml of dry isopropanol and isolated by filtration in the dry-box.

EXAMPLE 10

Copolymerization of 1-butene and Hexeny-9-BBN in Batch Reaction

Following procedures similar to those set forth in Example 7, 13.45 g (0.2401 mol) of dried 1-butene liquid at $-30°$ C. was transferred into a 500 ml schlenk flask containing 200 ml of degassed toluene. This reaction flask was then warmed to room temperature before being placed into a 49.03 g (0.2401 mol) of hexenyl-9-BBN was added via the side-arm bulb. Note that the reactor contained a negative pressure. The residual monomer was washed in with 10 ml of toluene. Meanwhile, 4.093 g ($5.585\times10^{-2}$ mole) of $AlEt_2Cl$ in 15 ml of toluene was added dropwise to the burgundy colored slurry of 15 ml toluene and 0.901 g ($5.97 \times 10^{-3}$ mol) of solid $TiO_3$ AA. This catalyst was premixed for ½ hour before being added to the reactor via the side-arm bulb. After 1 hour of polymerizing at room temperature, cold isopropanol (20 ml) was added to terminate the polymerization as shown by the color change from deep burgundy to clear, pale brown. The reactor contents were then poured into a bottle containing 300 ml of isopropanol. The polymer was isolated by filtration, washed with more isopropanol, and squeeze dried, all in the dry-box. The resulting polybutene (sample C2 in Table 3) contains about 37 mole % of borane groups. The same reaction was repeated with 25% borane monomer, resulting in the borane containing polybutene (C1) with 15% borane incorporation as shown in Table 3.

TABLE 3

Summary of Copolymerization of Borane Monomer and 1-butene in The Batch Reactions

| Copolymers | % B* in Feed | % B in Copolymer | Reaction Time (hr.) | Yield (%) |
|---|---|---|---|---|
| C1 | 25 | 15 | 1 | 64 |
| C2 | 50 | 37 | 1 | 58 |

*5-hexenyl-9-BBN

EXAMPLE 11

Copolymerization of 1-Butene and Hexeny-9-BBN in Continuous Reaction

In an argon filled dry-box, 15.477 g of 5-hexenyl-9-BBN and 200 ml of hexane were placed in a Parr 450 ml stirred pressure reactor and sealed. Outside the box, 18 g of 1-butene was added under $N_2$ pressure. A slurry of 1.027 g of $TiCl_3$.AA and 4.705 g of $AlEt_2Cl$ in 100 ml of toluene was then added under $N_2$ pressure to catalyze the copolymerization. Additional 1-butene was added at 30 minute intervals with 14 and 10 g being added at respective intervals. After the last monomer charge, the reaction was performed for an additional half hour before being terminated by injection of 50 ml of isopropanol. The reaction was stirred for additional ½ hour before being vented of excess pressure and being placed into the box for further purification with IPA. The resulting polybutene (sample D1 in Table 4) contains about 2.5 mole % of borane groups. The same reaction was repeated with 10 borane monomer to form the borane containing polypropylene (D2) having 6.5% borane incorporated therein.

TABLE 4

Summary of Copolymerization of 1-butene and borane Monomer by Continuous Reaction

| Sample number | % B* in Feed | % B in Polymer | Reaction Time(hr.) | Yield (%) |
|---|---|---|---|---|
| D1 | 5 | 2.5 | 2 | 70 |
| D2 | 10 | 6.5 | 2 | 66 |

EXAMPLE 12

Synthesis of Polypropylene-q-PMMA

In an argon filled dry-box, 0.692 g of poly(propylene-co-hexenyl-9-BBN) from Example 7 was placed in a suspension with 4.040 g of dry, degassed methylmethacrylate. The suspension was stirred for ½ hour to wet the polymer particles with MMA. The reaction flask containing the borane copolymer and MMA equipped with only a rubber septa was taken out of the dry-box. After 48 hours of stirring, the suspension had completely gelled into a slightly translucent rubbery material. The solid was washed with acetone in a Soxhlet extractor for 12 hours. Both acetone soluble and insoluble fractions were washed with MeOH before drying under vacuum. The acetone fraction yielded 0.275 g of PMMA as identified by H-NMR and FTIR. The acetone insoluble fraction of 1.906 g was a white powdery solid which was 66.7% PMMA and 33.3% PP by H-NMR (run in $d_{10}$-O-xylene at 90° C.)

EXAMPLE 13

Synthesis of Polypropylene-q-PMMA

In an argon filled dry-box, 0.692 g of poly(propylene-co-hexenyl-9-BBN) from Example 7 was placed in a suspension with 4.079 g of MMA and 7.42 g of THF. After stirring for ½ hour in the dry-box, the septa equipped flask was taken out of the box. Immediately 1 ml of $O_2$ was injected into the reaction flask. After 1 hour of stirring, another 1 ml of $O_2$ was added. After 24 hours of stirring, the polymer was isolated by precipitation into MeOH. The polymer was then washed with acetone in a Soxhlet extractor for 12 hours. The acetone soluble fraction yielded 0.423 g of PMMA (as shown by $^1$H-NMR and FTIR). The acetone insoluble fraction yielded 1.496 g of white solid after drying under vacuum which was 52% PMMA and 48% PP by $^1$H-NMR (run in $d_{10}$-O-xylene at 120° C.).

EXAMPLE 14

Synthesis of Polypropylene-q-PMMA

In the dry box, 0.691 g of poly(propylene-co-hexenyl-9-BBN) from Example 7 was placed in suspension in 4.073 g MMA (dry, degassed). The suspension of fine white particles was stirred in the dry box. After 48 hours, suspension had formed a translucent, highly viscous gel. The polymer gel was washed with acetone in a Soxhlet extractor for 12 hours. Both the acetone soluble and insoluble fractions were washed with MeOH before drying under vacuum. The acetone soluble fraction yielded 0.336 g of PMMA (as identified by FTIR and $^1$H-NMR in $CDCCl_3$). The acetone insoluble fraction yielded 0.830 g of white powder that was 5% PMMA and 95% PP by $^1$H-NMR (run in $d_{10}$-O-xylene at 120° C.).

EXAMPLE 15

Synthesis of Polypropylene-q-PMMA

The B1 sample in Example 8 was used to study free radical graft-from reactions. In each experiment, 2 g of borane-containing polypropylene with 0.5 mole % of borane groups, was placed in a suspension of 14 g dry uninhibited MMA with or without THF in a sealed, opaque flask. The reaction was initiated by injecting dry $O_2$ with various procedures shown in Table 5. After stirring the mixture at room temperature for the indicated reaction time, the reaction was terminated by removal of MMA and oxygen under vacuum. The polymer solid was then refluxed in 100 ml of methanol before distilling off 20 ml of methanol and isolating the polymer by filtration. The polymer was then fractionated by acetone-extraction in a Soxhlet apparatus for 24 hours. Both insoluble and soluble fractions were isolated by vacuum-removal of solvent. The acetone insoluble polymer was PP-g-PMMA, which was completely soluble in xylene at elevated temperatures. The acetone soluble polymer was mainly PMMA homopolymer. Table 5 summarizes the experimental results.

TABLE 5

Summary of PP-q-PMMA Graft Copolymers

| Sample number | $O_2$ (ml/hr.) | MMA/THF (g) | Reaction Time (hrs) | acetone soluble | acetone insoluble | * mole % MMA in copolymer |
|---|---|---|---|---|---|---|
| E1 | 1.5/12 | 14/0 | 48 | 0.705 | 8.968 | 66 |
| E2 | 3.0/1 | 14/0 | 2 | 0.120 | 2.251 | 6 |
| E3 | 6 at once | 14/0 | 48 | 0.049 | 2.052 | 1.5 |
| E4 | 1.5/3 | 14/34 | 12 | 0.152 | 5.342 | 52 |
| E5 | diffusion | 14/34 | 48 | 0.095 | 2.413 | 12 |

* acetone insoluble fraction, determinated by $^1H$ NMR spectra.

EXAMPLE 16

Synthesis of Polypropylene-q-Poly(t-butyl methacrylate)

In the argon filled dry box, 0.4 g of poly(propylene-co-hexenyl-9-BBN) from example 7 was placed in a suspension with 1.78 g of t-butyl methacrylate (dried over $CaH_2$ and vacuum distilled). After stirring for ½ hour in the dry-box, the septa equipped flask was taken out of the box and stirred at room temperature. Air was very slowly diffused into the flask. Within 8 hours, the suspension viscosity had increased noticeably. By 24 hours, the reaction was stopped and the suspension had become a translucent solid. The solid was broken up and stirred in MeOH for 1 hour and then filtered. The polymer was extracted with acetone in a Soxhlet extractor for 18 hours. The acetone soluble fraction yielded 0.199 g. The acetone insoluble fraction yielded 1.02 g of white solid after drying under vacuum.

EXAMPLE 17

Synthesis of Polypropylene-q-Poly(tbutylmethacrylate)

In this study, a hydroborated polypropylene with approximately 1.7 mole % 1-hexene-4-B-9-BBN units obtained from Example 9 was used. The t-butylmethacrylate monomer (t-BM) was purified by drying over calcium hydride and distilling under vacuum. The middle fraction was degassed and complexed with triethylaluminum. The monomer was used immediately or stored in the dry-box freezer at −20° C. for no more than 2 days.

In the dry box, 2.0 g of borane-containing PP powder and 35 ml of dry, degassed benzene were placed in a 100 ml flask and stirred overnight to swell the PP. After adding 3.50 g of t-butylmethacrylate to the polymer slurry the flask was wrapped in aluminum foil to exclude light from the reaction. The flask was sealed with a ground glass valve plugged at the other end with a rubber septum. The reaction was stirred for 8 hours before removing it from the dry box and injecting 0.9 ml of $O_2$ with a gas tight syringe. The ground glass valve on the adapter was opened and a needle was inserted through the rubber septa, through the open valve, and into the solution before injecting the gas. For the first 24 hours 0.9 ml of $O_2$ was added every 3 hours (after that the amount of $O_2$ per injection was increased and the time intervals increased), until after 60 hours a total of 18 ml of $O_2$ was added. The reaction was terminated by removing residual t-BM and benzene under vacuum. The product was swollen in degassed THF added via a cannula under $N_2$ pressure. The copolymer was cooled to 0° C. before being oxidated by the addition of 0.03 g of NaOH and 0.05 g $H_2O_2$ in 30 ml of cold THF. The solids were precipitated into MdOH and washed with hot water. The product was refluxed in MeOH before distilling off 20% of the alcohol to azeotrope out any residual $B(OH)_3$. The solid product was stirred in acetone for 24 hours and separated by centrifuging. The polymer was fractionated further with hot acetone in a Soxhelet extractor for 48 hours under $N_2$ bubbling. After isolation and drying, 3.656 g of acetone insoluble copolymer was recovered. The copolymer was PP-g-P(t-BM) comprising 29 mole % t-BM and 71 mole % propylene based on $^1H$ NMR. About 0.488 g of acetone soluble material was obtained.

EXAMPLE 18

Synthesis of Polypropylene-q-Poly(t-Butylmethacrylate-co-iso-Octylacrylate)

Tert-butyl methacrylate (t-BM) and iso-Octylacrylate (i-OA) monomers were purified by drying over calcium hydride and distilling under vacuum. The middle fraction of each was collected and stored in an argon filled dry box. The monomers were used immediately or stored in the dry-box freezer at −20° C. for no more than 2 days. The polymeric initiator was borane-containing polypropylene obtained from Example 9, containing 1.7 mole % 1-hexenyl-4-B-9-BBN units.

In the dry box, 2.0 g of borane-containing PP powder and 5.55 g of t-BM and 10.30 g of iso-octylacrylate were placed in an 100 ml flask and wrapped in aluminum foil to exclude light from the reaction. The flask was sealed with a ground glass valve plugged at the other end with a rubber septum. The reaction was stirred for 8 hours before removing it from the dry box and injecting 0.9 ml of $O_2$ with a gas tight syringe. For the first 24 hours 0.9 ml of $O_2$ was added every 3 hours (after that the amount of $O_2$ per injection was increased and the time intervals increased), until after 60 hours a total of 18 ml of $O_2$ had been added. The reaction was terminated by the addition of 0.03 g of NaOH and 0.05 g $H_2O_2$ in 30 ml of cold THF. The polymer was precipitated into MeOH and washed with hot water. The product was then refluxed in MeOH before distilling of 20% of the alcohol to azeotrope out any residual $B(OH)_3$. The polymer was fractionated with hot acetone in a Soxhelet for 48 hours under $N_2$ bubbling. After isolation and drying, 4.141 g of acetone insoluble and 3.021 g of acetone soluble material were obtained. Analysis by $^1H$ NMR of the acetone insoluble fraction in $d_{10}$-o-xylene at 130° C. indicated a copolymer consisting of 75.2 mole % PP, 13.0% i-OA, and 11.8% t-BM.

EXAMPLE 19

Synthesis of Polypropylene-q-Poly(vinyl acetate)

Vinyl acetate monomer (Aldrich) was purified by drying over calcium hydride and distilling under vacuum. The middle fraction was collected and stored in an argon filled dry box. The monomer was used immediately or stored in the dry box freezer at −20° C. for no more than 2 days. The polymeric initiator was borane-containing polypropylene obtained from Example 9, containing 1.7 mole % 1-hexenyl-4-B-9-BBN units. In the dry box, 2.0 g of borane-containing PP powder and 18.0 g of vinyl acetate were placed in a 100 ml flask and wrapped in aluminum foil to exclude light from the reaction. The flask was sealed with a ground glass valve plugged at the other end with a rubber septum. The reaction was stirred for 8 hours before removing it from the dry-box and injecting 0.9 ml of $O_2$ with a gas tight syringe. For the first 24 hours 0.9 ml of $O_2$ was added every 3 hours (after that the amount of $O_2$ per injection was increased and the time intervals increased), until after 60 hours a total of 18 ml of $O_2$ had been added. The reaction was terminated by removing the excess VAc monomer under vacuum. The solid product was refluxed in MeOH for 1 hour before distilling off 20% of the alcohol. The polymer was fractionated by refluxing in acetone for 3 hours, cooling to room temperature, and centrifuging. The acetone insoluble portion was extracted further with hot acetone in Soxhelet extractor for 48 hours under $N_2$ bubbling. After isolation and drying, 2.475 g of acetone soluble and 5.3 g of acetone soluble material were obtained. $^1H$ NMR in $d_{10}$-o-xylene of the acetone insoluble fraction indicated by integration that the material was 16 mole % VAc and 84% PP.

EXAMPLE 20

Synthesis of Polyethylene-q-PMMA

The starting material was the unsaturated poly(propylene-co-1,4-hexadiene), containing 1.5 mole % of 1,4-hexadiene, which prepared by Ziegler-Natta polymerization. In an argon filled dry box, 1 g of inhibitor-free poly(ethylene-co-1,4-hexadiene) was placed in a suspension of 30 ml of dry, degassed toluene. A solution of 0.12 g of 9-BBN in 15 ml of dry, degassed THF was added to the polymer suspension. The suspension was heated to 65° C. in a flask equipped with a condenser. After stirring for 5 hours, the polymer was precipitated into 150 ml of dry, degassed isopropanol and isolated by filtration in the dry box.

The hydroborated polyethylene was then placed in a suspension of 5 g dry uninhibited MMA with 10 ml of THF in a sealed, opaque flask. About 0.8 ml of $O_2$ was injected into the reaction flask.

After one hour of stirring, another 0.8 ml of $O_2$ was added. The same procedure was repeated 5 times. The solution was stirred at room temperature for 24 hours before removing out unreacted MMA and oxygen under vacuum. The polymer solid was than refluxed in 100 ml of methanol before distilling off 20 ml of methanol and isolating by filtration. The polymer was then fractionated by acetone-extraction in a Soxhlet apparatus for 24 hours. Both insoluble and soluble fractions were isolated by vacuum-removal of solvent. The acetone insoluble polymer was about 3.8 g, which is PE-g-PMMA copolymer with ethylene/MMA mole ratio of 59/41 based on the $^1H$ NMR studies.

EXAMPLE 21

Synthesis of Polyethylene-q-PMMA

The starting material was a high density and molecular weight polyethylene (PE) with an unsaturation in each polymer chain. The polymer was prepared by Ziegler-Natta polymerization with the $\beta$-proton elimination as the major termination process. In a dry-box, about 1 g of inhibitor-free PE was placed in a suspension of 30 ml of dry toluene. A solution of 0.05 g of 9-BBN in 15 ml of dry THF was added to the polymer suspension. The suspension was heated to 65° C. in a flask equipped with a condenser. After stirring for 5 hours, the polymer was precipitated into 150 ml of dry, degassed isopropanol and isolated by filtration in the dry box. The hydroborated polyethylene was then placed in a suspension of 15 g dry uninhibited MMA in a opaque flask with a tight rubber septum. A graft-from reaction was performed by stirring the solution at room temperature for 5 days. No oxygen was intentionally added to the system. However, it was believed that a small quantity of oxygen was diffused into the flask during the long reaction time, which was sufficient to oxidize the borane groups attached to the polyethylene backbone. After removing out unreacted MMA, the polymer was fractionated by acetone-extraction in a Soxhlet apparatus for 24 hours. Both insoluble and soluble fractions were isolated by vacuum-removal of solvent. The acetone insoluble polymer comprised about 2.65 g with an ethylene/MMA mole ratio of 65/35 based on the $^1H$ NMR studies.

EXAMPLE 22

Hydroboronation of Poly(isobutylene-co-isoprene)

Under atmosphere, 0.6 g of commercial butyl rubber, poly(isobutylene-co-isoprene) containing 1.6 mole % of isoprene, was dissolved in 30 ml of THF solvent. The hydroboronation reaction was completed by adding 0.013 g of 9-BBN crystal to the solution, then refluxing at 68° C. for 10 hours. The resulting hydroboronated butyl rubber in TttF solution was used directly for graft reactions to prepare butyl rubber graft copolymers as described below.

EXAMPLE 23

Synthesis of Poly(isobutylene-co-isoprene)-q-Polystyrene

In an argon filled dry box 0.6 g of poly(isobutylene-co-isoprene) containing 1 mole % of borane groups in THF solution obtained from Example 12, was mixed with 10 g of styrene. After stirring for ½ hour in the dry-box, the septa equipped flask was taken out of the box. Immediately 7 ml of $O_2$ was injected into the reaction flask. After 4 hours of stirring, another 5 ml of $O_2$ was added. The solution was stirred at room temperature for 70 hours. The polymer was isolated by precipitation into MeOH, which was then washed with ethyl acetate in Soxhlet extractor for 12 hours. The resulting graft copolymer after drying under vacuum overnight was 0.84 g, which had the composition of 30/70 mole ratio between polystyrene and poly(isobutylene-co-isoprene)

EXAMPLE 24

Synthesis of Poly(isobutylene-co-isoprene)-q-PMMA

In an argon filled dry-box, 0.6 g of poly(isobutylene-co-isoprene)containing 1 mole % of borane groups in THF solution obtained from Example 12, was mixed with 10 g of methyl methacrylate. After stirring for ½ hour in the dry box, the septa equipped flask was taken out of the box. Immediately 7 ml of $O_2$ was injected into the reaction flask. After 4 hours of stirring, another 5 ml of $O_2$ was added. The solution was stirred at room temperature for 45 hours. The polymer was isolated by precipitation into MeOH, which was then washed with acetone in a Soxhlet extractor for 12 hours. The acetone soluble fraction yielded 0.54 g of graft copolymer with high concentration of PMMA. The acetone insoluble fraction yielded 1.07 g of white solid after drying under vacuum. The composition had a 46/54 mole ratio between PMMA and poly(isobutylene-co-isoprene) by $^1H$-NMR studies.

EXAMPLE 25

Hydroboration of Poly(ethylene-co-propylene-co-1,4-hexadiene

In a typical hydroboration reaction, 3 g of EP rubber containing 1.6 mole % of 1,4-hexadiene was dissolved in 140 ml of THF solvent. The hydroboration reaction was performed by adding 0.16 g of 9-BBN crystal to the solution under inert atmosphere. After refluxing at 65° C. for 5 hours, the hydroborated EP polymer was precipitated by adding 150 ml of isopropanol, then isolated by filtration. In some cases, especially when less than the stoichiometric amount of 9-BBN (vs. double bonds) was added, the resulting hydroborated polymer in THF solution was used directly for graft-from reaction to prepare EP graft copolymers.

unreacted oxygen and then precipitating the resulting polymer in 30 ml of isopropanol. For the complete removal of borane groups, the polymer was redissolved in 30 ml of THF and reacted with 25 mg of NaOH which was dissolved in the mixed solvent (water/methanol/THF=1:1:2) and 110 mg of $H_2O_2$ (30% in water). After reacting at ambient temperature for 3 hours, the polymer was precipitated into 30 ml of isopropanol. The extraction processes were carried out by stirring polymer in hexane and acetone solvents for 24 hours, respectively. After solvent-removal, three fractions were dried in vacuum oven at 40° C. for 24 hours. The hexane and acetone insoluble fraction (but soluble in THF) yielded 1.229 g of graft copolymer with 35/65 mole ratio between PMMA and EP by $^1$H-NMR measurement. The experimental results is summarized in sample F2 of Table 6.

TABLE 6

Summary of EP-q-PMMA Copolymers Prepared by EP Rubber of Example 25*

| Sample number | 9-BBN/Olefin | MMA (g) | O2/9-BBN | Hexane Sol.(g) | Acetone Sol. (g) | Insoluble** Fraction(g) | % PMMA in EP-G-PMMA |
|---|---|---|---|---|---|---|---|
| F1 | 2/1 | 14 | 1/2 | 0.038 | 0.473 | 2.001 | 52 |
| F2 | 211 | 7 | 1/2 | 0.041 | 0.142 | 1.229 | 35 |
| F3 | 1/1 | 7 | 1/2 | 0.112 | 0.243 | 0.992 | 28 |
| F4 | 1/1 | 7 | 1/2*** | 0.060 | 0.487 | 0.993 | 32 |
| F5 | 0.5/1 | 7 | 1/2 | 0.119 | 0.246 | 0.889 | 28 |

* All graft-from reactions were run by using 0.75 g of poly (ethylene-co-propylene-co-1,4-hexadiene) in of THF solvent. The oxygen was slowly introduced to the reaction solution, 10% of oxygen hourly, at ambient temperature.
** Samples are soluble in THF.
*** The graft-from reaction were carried out at 55° C.

EXAMPLE 26

Hydroboration of Poly(ethylene-co-propylene-co-5-ethylidene-2-norbornene

Following a similar hydroboration procedure as set forth in Example 25, 3 g of EP rubber containing about 1.5 mole % of 5-ethylidene-2-norbornene was dissolved in 140 ml of THF solvent. The hydroboration reaction was performed by adding 0.16 g of 9-BBN crystal to the solution under inert atmosphere. After refluxing at 65° C. for 5 hours, the hydroborated EP polymer was precipitated by adding 150 ml of isopropanol, then isolated by filtration. To measure the concentration of 9-BBN in the polymer, the hydroborated product was oxidized to hydroxy polymer by reacting with $NaOH/H_2O_2$. The reaction took place at ambient temperature for 3 hours before precipitating in methanol. The hydoxylated polymer was purified by redissolving in THF and reprecipitating in methanol twice before drying in a vacuum oven at 40° C. for 24 hours. The $_1$H NMR spectrum indicates 94% of double bonds have been converted to hydroxy groups.

EXAMPLE 27

Synthesis of EP-q-PMMA

In an argon filled dry-box, 0.75 g of borane containing EP rubber prepared in Example 25, dissolved in about 80 ml THF, was mixed with 7 g of methyl methacrylate in a reaction flask equipped with a high vacuum stopcock. After stirring for ½ hour in the dry-box, the flask was taken out and connected to a vacuum line. About 0.8 ml of $O_2$ was introduced into the reaction flask through the vacuum line. After one hour of stirring, another 0.8 ml of $O_2$ was added. The same procedure was repeated 5 times. The solution was stirred at room temperature for 24 hours before pumping out

EXAMPLE 28

Synthesis of EP-q-PMMA

Following similar experimental procedures as in Example 27, borane containing EP rubber obtained from Example 26 was examined in the graft reaction. In a typical experiment (sample G1), 0.75 g of borane containing EP rubber dissolved in 80 ml THF was mixed with 14 g of methyl methacrylate in a reaction flask equipped with a high vacuum stopcock. After stirring for ½ hour in the dry-box, the flask was taken out and connected to a vacuum line. About 0.8 ml of $O_2$ was introduced into the reaction flask through the vacuum line. After one hour of stirring, another 0.8 ml of $O_2$ was added. The same procedure was repeated 5 times. The solution was stirred at room temperature for 24 hours before pumping out unreacted oxygen and then precipitating the resulting polymer in 30 ml of isopropanol. For the complete removal of borane groups, the polymer was redissolved in 30 ml of THF and reacted with 25 mg of NaOH which was dissolved in the mixed solvent (water/methanol/THF=1:1:2) and 110 mg of $H_2O_2$ (30% on water). After reacting at ambient temperature for 3 hours, the polymer was precipitated into 30 ml of isopropanol. The extraction processes were carried out by stirring the polymer in hexane and acetone solvents for 24 hours, respectively. After solvent-removal, three fractions were dried in vacuum oven at 40° C. for 24 hours. The hexane and acetone insoluble fraction (but soluble in THF) yielded 1.259 g of graft copolymer with 51/49 mole ratio between PMMA and EP by $^1$H-NMR measurement. A series of experiments were made using a similar reaction scheme. The reaction conditions and results are summarized in Table 7.

TABLE 7

Summary of EP-q-PMMA Copolymers Prepared by EP Rubber of Example 27*

| Sample number | 9-BBN/Olefin | MMA (g) | O2/9-BBN | Hexane Sol.(g) | Acetone Sol. (g) | Insoluble** Fraction(g) | % PMMA in EP-G-PMMA |
|---|---|---|---|---|---|---|---|
| G1 | 2/1 | 14 | 1/2 | 0.138 | 1.194 | 1.259 | 51 |
| G2 | 2/1 | 7 | 1/2 | 0.083 | 0.118 | 1.016 | 28 |
| G3 | 2/1 | 7 | 1/1 | 0.155 | 0.327 | 0.949 | 34 |
| G4 | 1/1 | 7 | 1/2 | 0.092 | 0.216 | 0.957 | 25 |

* All graft-from reactions were run by using 0.75 g of poly (ethyleneborene) in 80 g of THF. The oxygen was slowly introduced to the reaction solution, 10% hourly, at ambient temperature.
** Samples are soluble in THF.

What is claimed is:

1. A process for preparing a graft copolymer having the formula I

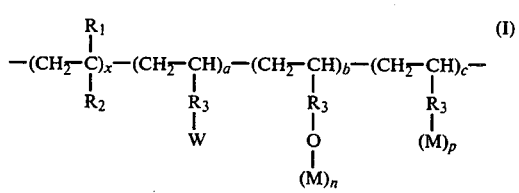

wherein $R_1$ and $R_2$ are the same or different and are selected from H, $C_1$ to $C_{20}$ linear or branched alkyl, phenyl and alkyl substituted phenyl; $R_3$ is a direct linkage or a divalent linear or branched hydrocarbon having from 1 to 20 carbon atoms; W is a polar substituent; M is the residue of a free radically polymerizable monomer; n and p are the same or different and are the degree of polymerization of M ranging from 1 to about 70,000; $(M)_n$ and $(M)_p$ comprise polymer segments chemically bonded as side chains or chain ends; x ranges from about 50 to about 70,000; (a) ranges from 0 to 20,000; (b) ranges from 1 to about 20,000; (c) ranges from 0 to about 20,000; and the sum of (b)+(c) ranges from at least 1 to about 20,000, which comprises:

(i) contacting in the presence of a Ziegler-Natta polymerization catalyst a mixture of at least one $C_2$ to $C_{22}$ alpha-monoolefin and a borane-containing monomer having the structure $CH_2=CH(CH_2)_m-BR_4R_5$, wherein m is an integer ranging from 3 to 12 and $R_4$ and $R_5$ are the same or different and are selected from the group consisting of $C_1$ to $C_{10}$ alkyl groups and C to $C_{10}$ cycloalkyl groups;

(ii) subjecting the mixture from step (i) to polymerization conditions to form a copolymer product containing borane units;

(iii) contacting the copolymer of step (ii) with at least one free radically polymerizable monomer in the presence of a free radical catalyst capable of converting said borane units into free radicals; and (iv) subjecting the mixture of step (iii) to free radical polymerization conditions to convert at least a portion of said borane units to free radicals and to thereby initiate graft polymerization and the formation of a graft copolymer product containing polymeric side chains based on said free radically polymerizable monomer.

2. The process of claim 1, wherein (a) ranges from 0 to about 100, (b) ranges from 1 to about 100, and c ranges from about 0 to about 100.

3. The process of claim 2, wherein said borane-containing monomer is selected from the group consisting of B-(7-octen1-yl)-9-BBN, B-(5-hexen-1-yl)-9-BBN and B-(4-penen-1-yl)-9-BBN.

4. The process of claim 3, wherein said free radical catalyst comprises an oxidative reagent.

5. The process of claim 14, wherein said free radical catalyst is selected from the group consisting of oxygen and air.

6. The process of claim 5, wherein said $C_2$ to $C_{22}$ monoolefin is selected from the group consisting of ethylene, propylene, 1-butene, 1-octene, isobutylene and mixtures thereof.

7. The process of claim 6, wherein said monoolefin is propylene.

8. The process of claim 6, wherein said monoolefin is 1-octene.

9. The process of claim 6, wherein said monoolefin comprises a mixture of ethylene and propylene.

10. The process of claim 2, wherein said free radical catalyst comprises an oxidative reagent.

11. The process of claim 10, wherein said free radical catalyst is selected from the group consisting of oxygen and air.

12. The process of claim 11, wherein said $C_2$ to $C_{22}$ monoolefin is selected from the group consisting of ethylene, propylene, 1-butene, 1-octene, isobutylene and mixtures thereof.

13. The process of claim 1, wherein said borane-containing monomer is selected from the group consisting of B-(7-octene1-yl)-9-BBN, B-(5-hexen-1-yl(-9-BBN and B-(4-penen-1-yl)-9-BBN.

14. The process of claim 13, wherein said free radical catalyst comprises an oxidative reagent.

15. The process of claim 14, wherein said free radical catalyst is selected from the group consisting of oxygen and air.

16. The process of claim 1, wherein said free radical catalyst comprises an oxidative reagent.

17. The process of claim 16, wherein said free radical catalyst is selected from the group consisting of oxygen and air.

18. The process of claim 17, wherein said $C_2$ to $C_{22}$ monoolefin is selected from the group consisting of ethylene, propylene, 1-butene, 1-octene, isobutylene and mixtures thereof.

19. The process of claim 1, wherein said $C_2$ to $C_{22}$ monoolefin is selected from the group consisting of ethylene, propylene, 1-butene, 1-octene, isobutylene and mixtures thereof.

20. The process of claim 1, wherein said monoolefin is propylene.

21. The process of claim 1, wherein said monoolefin is 1-octene.

22. The process of claim 1, wherein said monoolefin comprises a mixture of ethylene and propylene.

23. The process of claim 1, wherein said free radically polymerizable monomer is selected from the group consisting of alkyl acrylates and methacrylates, acrylic and methacrylic acid, vinyl aromatic compounds, vinyl amides, vinyl pyridines, acrylonitriles, vinyl acetates, vinyl or vinylidene chloride and mixtures thereof.

24. The process of claim 1, wherein said graft copolymer is further reacted with a reagent to introduce at least one polar functional group into the polymer chain.

25. The process of claim 24, wherein said functional group is selected from the group consisting of NH$_2$, CHO, OH and halogen.

26. A process for preparing a graft copolymer having a formula selected from formulas II and III:

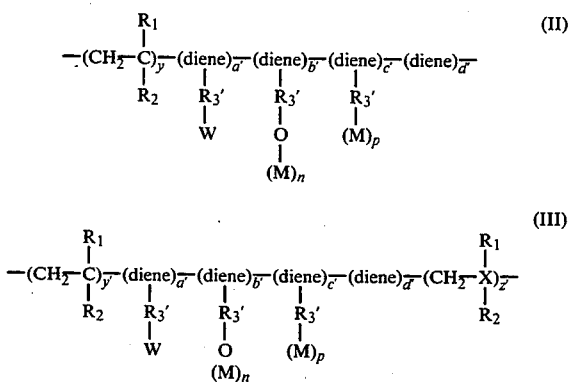

wherein R$_1$ and R$_2$ are the same or different and are selected from H, C$_1$ to C$_{20}$ linear or branched alkyl, phenyl and alkyl substituted phenyl; R$_3'$ is a direct link or a linear, cyclic, or branched hydrocarbon having from 1 to 20 carbon atoms; (diene) is a recurring segment of a polymerized diolefin monomer; W is a polar substituent; M is the residue of a free radically polymerizable monomer; n and p are the same or different and are the degree of polymerization of M ranging from 1 to about 70,000; y ranges from 0 to about 70,000; (a') ranges from 0 to about 20,000; (b') ranges from 1 to about 20,000; (c') ranges from 0 to about 20,000; (d') ranges from about 0 to about 70,1000; y' and z' are the same or different and range from about 100 to about 50,000; and the sum of (b')+(c') ranges from at least 1 to about 20,000, which comprises:

(i) contacting a backbone polymer selected from the group consisting diene homopolymer and diene copolymer derived from diene monomer and at least one C$_2$ to C$_{22}$ monoolefin monomer with a hydroboronation reagent under hydroboronation conditions to incorporate borane groups on the backbone polymer;

(ii) contacting the borane-group containing polymer of step (i) with at least one free radically polymerizable monomer in the presence of a free radical catalyst capable of converting said borane groups to free radicals;

(iii) subjecting the mixture of step (ii) to free radical polymerization conditions to convert at least a portion of said borane groups to free radicals and to thereby initiate graft polymerization and the formation of a graft copolymer product containing polymeric side chains based on said free radically polymerizable monomer.

27. The process of claim 26, wherein said free radical catalyst comprises an oxidative reagent.

28. The process of claim 27, wherein said free radical catalyst is selected from the group consisting of oxygen and air.

29. The process of claim 28, wherein said backbone polymer is selected from the group consisting of polybutadiene, poly(styrene/butadiene/styrene), poly(styrene/isoprene/styrene), isobutylene/isoprene copolymers, and terpolymers of ethylene/propylene and non-conjugate diene.

30. The process of claim 28, wherein said monoolefin is isobutylene and air diene is isoprene.

31. The process of claim 28, wherein said monoolefin is a mixture of ethylene and propylene and said diene is a non-conjugated diene.

32. The process of claim 26, wherein the graft copolymer product has the formula II and wherein y is 0.

33. The process of claim 32, wherein (a') ranges from 0 to about 100, (b') ranges from 1 to about 100, and the sum of (b')+(c') ranges from 1 to about 100.

34. The process of claim 32, wherein said free radical catalyst is selected from the group consisting of oxygen and air.

35. The process of claim 26, wherein the graft copolymer product has the formula II and wherein y is at least 1.

36. The process of claim 35, wherein said free radical catalyst is selected from the group consisting of oxygen and air.

37. The process of claim 36, wherein said C$_2$ to C$_{22}$ monoolefin is selected from the group consisting of ethylene, propylene, 1-butene, 1-octene, isobutylene and mixture thereof.

38. The process of claim 37, wherein said monoolefin is isobutylene and said diene monomer is isoprene.

39. The process of claim 36, wherein R$_2$ is selected from phenyl and alkyl substituted phenyl and R$_1$ is H.

40. The process of claim 39, wherein R$_2$ is selected from phenyl and alkyl substituted phenyl and R$_1$ is H.

41. The process of claim 35, wherein (a') ranges from 0 to about 100, (b') ranges from 1 to about 100, and the sum of (b')+(c') ranges from 1 to about 100.

42. The process of claim 26, wherein the graft copolymer has the formula III.

43. The process of claim 42, wherein said free radical catalyst is selected from the group consisting of oxygen and air.

44. The process of claim 43, wherein said C$_2$ to C$_{22}$ monoolefin is selected from the group consisting of ethylene, propylene, 1-butene, 1-octene, isobutylene and mixtures thereof.

45. The process of claim 44, wherein said monoolefin is isobutylene and said diene monomer is isoprene.

46. The process of claim 26, wherein said backbone polymer is selected from the group consisting of polybutadiene, poly(styrene/butadiene/styrene), poly(styrene/isoprene/styrene), isobutylene/isoprene copolymers, and terpolymers of ethylene/propylene and a non-conjugate diene.

47. The process of claim 26, wherein said free radically polymerizable monomer is selected from the group consisting of alkyl acrylates and methacrylates, acrylic and methacrylic acid, vinyl aromatic compounds, vinyl amides, vinyl pyridines, acrylonitriles, vinyl acetates, vinyl or vinylidene chloride and mixtures thereof.

48. The process of claim 26, wherein said graft copolymer is further reacted with a reagent to introduce at least one polar functional group into the polymer chain.

49. The process of claim 48, wherein said functional group is selected from the group consisting of NH$_2$, CHO, OH and halogen.

50. A graft copolymer prepared in accordance with the process of claim 26, wherein (d') in formula II is from 1 to about 70,000.

51. The graft copolymer of claim 50, wherein said graft copolymer has the formula II and wherein the y units are derived from a monoolefin selected from the group consisting of ethylene, propylene, 1-butene, 1-octene, isobutylene, styrene, alpha-methylstyrene and mixtures thereof.

52. The graft copolymer of claim 50, wherein said graft copolymer has the formula III and wherein the y' units are derived from a monoolefin selected from the group consisting of ethylene, propylene, 1-butene, 1-octene, isobutylene, styrene, alpha-methylstyrene and mixtures thereof.

53. The graft copolymer of claim 50, wherein said graft copolymer has the formula II and wherein the y units are derived from a mixture of ethylene and propylene and the diene units are derived from isoprene.

54. The graft copolymer of claim 50, wherein said graft copolymer has the formula III and wherein the y' units are derived from a mixture of ethylene and propylene and the diene units are derived from isoprene.

55. The graft copolymer of claim 50, wherein said graft copolymer has the formula II and wherein the y units are derived from a mixture of ethylene and propylene and the diene units are derived from a non-conjugated diolefin.

56. The graft copolymer of claim 50, wherein said graft copolymer has the formula III and wherein the y' units are derived from a mixture of ethylene and propylene and the diene units are derived from a non-conjugated diolefin.

57. The graft copolymer of claim 50, wherein y is 0.

58. The graft copolymer of claim 57, wherein said M units are based on a free radically polymerized monomer selected from the group consisting of alkyl acrylates and methacrylates, acrylic and methacrylic acid, vinyl aromatic compounds, vinyl amides, vinyl pyridines, acrylonitriles, vinyl acetates, vinyl or vinylidene chloride and mixtures thereof.

59. The graft copolymer of claim 50, wherein said M units are based on a free radically polymerized monomer selected from the group consisting of alkyl acrylates and methacrylates, acrylic and methacrylic acid, vinyl aromatic compounds, vinyl amides, vinyl pyridines, acrylonitriles, vinyl acetates, vinyl or vinylidene chloride and mixtures thereof.

* * * * *